(12) United States Patent
Church et al.

(10) Patent No.: US 6,501,984 B1
(45) Date of Patent: Dec. 31, 2002

(54) ELECTRICAL IMPEDANCE TOMOGRAPHY METHOD AND ELECTRODE ARRANGEMENT FOR USE THEREIN

(75) Inventors: Philip M. Church, Kanata; Philip M. Wort, Ottawa, both of (CA)

(73) Assignee: Computing Devices Canada Ltd., Neapean (CA)

( * ) Notice: Subject to any disclaimer, the term of this patent is extended or adjusted under 35 U.S.C. 154(b) by 0 days.

(21) Appl. No.: 09/308,521

(22) PCT Filed: Nov. 25, 1997

(86) PCT No.: PCT/CA97/00876

§ 371 (c)(1),
(2), (4) Date: May 20, 1999

(87) PCT Pub. No.: WO98/23204

PCT Pub. Date: Jun. 4, 1998

(30) Foreign Application Priority Data

Nov. 26, 1996 (CA) .............................................. 2191285

(51) Int. Cl.[7] ................................................. A61B 5/05

(52) U.S. Cl. ...................................................... 600/547

(58) Field of Search ............................... 600/547, 407, 600/393; 324/600, 603, 605, 609, 629

(56) References Cited

U.S. PATENT DOCUMENTS

| | | | |
|---|---|---|---|
| 4,617,939 A | 10/1986 | Brown et al. ................. | 128/734 |
| 5,284,142 A | 2/1994 | Goble et al. ............. | 128/653.1 |
| 5,311,878 A | 5/1994 | Brown et al. ................. | 128/734 |
| 5,351,697 A | 10/1994 | Cheney et al. ................ | 128/734 |
| 5,381,333 A | 1/1995 | Isaacson et al. ........ | 364/413.13 |
| 5,465,730 A | 11/1995 | Zadehkoochak et al. ..... | 128/734 |
| 5,807,251 A | * 9/1998 | Wang et al. ................. | 600/407 |
| 5,919,142 A | * 7/1999 | Boone et al. ................ | 600/547 |

FOREIGN PATENT DOCUMENTS

| | | | | |
|---|---|---|---|---|
| GB | 2 138 148 | 10/1984 | ............. | A61B/5/05 |
| GB | 2 257 530 | 1/1993 | ............. | A61B/5/05 |
| GB | 2 272 772 | 5/1994 | ............. | A61B/5/05 |
| WO | WO 93/00038 | 1/1993 | ............. | A61B/5/05 |
| WO | WO 95/24155 | 9/1995 | ............. | A61B/5/05 |
| WO | WO 97/40743 | 11/1997 | ............. | A61B/5/05 |

OTHER PUBLICATIONS

"A Comparison of Three Electrode Configurations for Electrical Impedance Tomography", by M.J. Booth et al, The Institution of Electrical Engineers, 1995.

"A data collection system for gathering electrical impedance measurements from the human breast", by R. Skidmore et al, Clin. Phys. Physiol. Meas., 1987, vol. 8, Suppl. A, 99–102.

"An Application of Electrocardiographic Lead Theory to Impedance Plethysmography", by David B. Geselowitz, IEEE Transactions on Bio–medical Engineering, vol. BME–18, No. 1, Jan. 1971, 38–41.

(List continued on next page.)

*Primary Examiner*—George Manuel
(74) *Attorney, Agent, or Firm*—Thomas Adams (57) ABSTRACT

An electrode arrangement for an electrical impedance tomography system comprises a plurality of electrodes in an array mounted in a support medium for supporting the electrodes adjacent a surface of a volume the electrical conductivity distribution of which is to be measured, for example the thorax or another body part, a pipeline, the ground, and so on. The electrodes are disposed in two groups, the arrangement being such that, in use, one group will be closer to the surface than the other group, In operation, applying a known current to them. For each stimulated pair, a resulting potential difference will be recorded at the pair of the remaining electrodes which, if stimulated, would produce an electric field with vectors of the electric field produced by the stimulated pair of electrodes.

53 Claims, 8 Drawing Sheets

OTHER PUBLICATIONS

"An Experimental Study in Electrical Impedance Tomography Using Backprojection Reconstruction", by Robert Guardo et al, IEEE Transactions on Biomedical Engineering, vol. 38, No. 7, Jul. 1991, 617–627.

"A sensitivity coefficient method for the reconstruction of electrical impedance tomograms", C.J. Kotre, Clin. Phy. Physiol. Meas., 1989, vol. 10, No. 3, 275–281.

"Electrical Impedance Computed Tomography Based on a Finite Element Model", by Tadakuni Murai et al, IEEE Transactions on Biomedical Engineering, vol. BME–32, No. 3, Mar. 1985, 177–184.

"Impedance Tomography: Computational Analysis Based on Finite Element Models of a Cylinder and a Human Thorax", by A. Vahid Shahidi et al, Annals of Biomedical Engineering, vol. 23, 61–69, 1995.

"A Vector Derivation Useful in Impedance Plethysmographic Field Calculations", by John Lehr, IEEE Transactions on Biomedical Engineering, Mar. 1972, 156–157.

"Skin impedance measurements using simple and compound electrodes", by E.J. Woo et al. Medical & Biological Engineering & Computing, vol. 30, No. 1, Jan. 1992, 97–102.

"Using Compound Electrodes in Electrical Impedance Tomography", by Ping Hua et al, IEEE Transactions on Biomedical Engineering, vol. 40, No. 1, Jan. 1993, 29–34.

* cited by examiner

ELECTRICAL IMPEDANCE TOMOGRAPHY METHOD AND ELECTRODE ARRANGEMENT FOR USE THEREIN

TECHNICAL FIELD

The invention relates to a method of performing electrical impedance tomography measurements and electrode arrangements for use therein.

The invention is applicable generally to the imaging of electrical impedance variations in conductive media, and especially in volume conductors such as parts of the human body, the ground, pipelines, and so on.

BACKGROUND ART

Electrical impedance tomography (EIT), also known as "applied potential tomography" (APT), is used to provide images of spatial variations in electrical impedance within a conductive volume conductor. The electrical impedance changes are measured by providing an array of electrodes about the volume to be imaged. A stimulus current is supplied to each pair of electrodes in turn and the resulting potential differences recorded between pairs of the remaining electrodes. The process is repeated until all of the independent combinations of stimulation/recording are exhausted. The measurements are used to determine the transfer impedance changes and construct an image of the volume. In contrast to X-ray computer tomography applications, where the paths of photons through a body are straight lines, the current paths in EIT are functions of an unknown electrical conductivity distribution. This gives rise to a non-linear image reconstruction problem. Nevertheless, algorithms have been devised for converting the series of measurements into an image of the electrical impedance distribution within the body at a sufficiently high rate that changes associated with respiratory and cardiac functions, for example, can be monitored.

The quality of the image depends upon the sensitivity of the measuring system, which typically varies with distance from the electrodes. In clinical applications, for example, where the electrodes are distributed around the body part to be measured, such as the thorax, difficulties may be encountered in resolving impedance changes which occur deep in the body. Most attempts to improve image quality have focused upon the reconstruction algorithms, as disclosed, for example, in U.S. Pat. Nos. 4,617,939, 5,381,333 and 5,465,730. Limited attention has been devoted to the electrode arrangement. For example, a study of various electrode configurations was described by Booth et al. in "A Comparison of Three Electrode Configurations for Electrical Impedance Tomography", IEE Colloquium on "Innovation in Instrumentation for Electrical Tomography", pp. 11/1, 11/3, 1995. British patent application number 2,257,530 disclosed electrodes in a circular array or "rosette" placed upon a substantially flat part of the body, such as the chest. This was said to be especially desirable when imaging the heart, since impedance changes occurring in the heart during the cardiac cycle will be larger than those occurring in the region of the skin.

Little attention has been paid to the way in which the measurements themselves are made. There are two kinds of procedure for taking the measurements. One involves applying stimulation currents simultaneously to a ring of electrodes to generate a current pattern and simultaneously measuring the corresponding voltage distribution around the same or adjacent electrodes. An example of such an approach is described in an article by P. Hua et al. entitled "An Electrical Impedance Tomograph using Compound Electrodes", presented at the IEEE Engineering in Medicine & Biology Society 11th. Annual International Conference, 1989. Hua et al. described experiments with thirty-two compound electrodes encircling a body to be measured. Each compound electrode comprised an inner electrode surrounded by an outer electrode with an annular space between them. In some cases, Hua et al. short-circuited the inner and outer electrodes and used them for both stimulation and recording. In other cases, Hua et al. injected a spatially-sinusoidal current pattern into the ring of 32 outer electrodes and recorded the corresponding generally sinusoidal voltage distribution around the ring of 32 inner electrodes. This approach requires 32 adjustable current generators which must be adjusted individually to give the required pattern as accurately as possible, making it difficult to obtain repeatable measurements accurately. Also, the equipment is complex and costly.

An example of the other kind of procedure is described in U.S. Pat. No. 4,617,939 (Brown et al.) issued October 1986. Brown et al. describe positioning 16 electrodes around a body, applying a current to a first pair of the electrodes and recording the potential difference between every other pair of the remaining electrodes. As also noted by Hua et al. (supra), significant contact impedance between the electrodes and the body surface militates against measurement sensitivity, so Brown et al. avoid using the same electrode for both stimulation and recording. Brown et al. repeat the procedure, applying current to pair of electrodes in turn. For each pair, Brown et al. measure voltages at all of the remaining electrodes. In practice, such a procedure would not be entirely satisfactory because many of the voltage measurements would be comparable with noise levels.

The present invention seeks to mitigate the disadvantages of these known EIT systems and provide an improved electrical impedance tomography procedure with enhanced sensitivity to changes in the electrical conductivity distribution inside the body of interest.

DISCLOSURE OF INVENTION

According to one aspect of the invention, a method of determining electrical impedance tomography of a conductive volume comprises the steps of selecting, in turn, each of a plurality of pairs of locations upon a surface of the conductive volume, supplying a stimulation current to the surface by way of the selected pair of locations, and recording, for each selected pair of locations, a resulting potential difference between at least one pair of the remaining locations, characterized in that, the steps of, for a particular pair of locations stimulated, selecting from among the remaining locations, for recordal, the pair or pairs of locations which, if stimulated, would produce an electric field with vectors most closely aligned with the corresponding vectors of the electric field produced by stimulation of said particular pair of locations, and recording said potential difference at the or each said pair of locations so selected for recordal.

The above method may be performed using a plurality of electrode means, each disposed upon or adjacent said surface at a respective one of said plurality of locations, each electrode mean being used to apply stimulation current to, or record potential at, said respective one of said locations.

Each electrode means may comprise two electrodes, that are closely located spatially, one for stimulation and the other for recording. One electrode may be disposed inside the other in a plane which, in use, will be parallel to the said surface. The stimulation current could then be applied to two outer electrodes and the potential difference measured at a said selected pair comprising the corresponding two inner electrodes. Conversely, the stimulation current could be applied to the two inner electrodes and the potential difference remeasured at the corresponding outer electrodes.

Alternatively, each electrode means may comprise a first electrode and a second electrode spaced apart from each other in a direction which, in use, will be substantially normal to the said surface. The stimulation current could be applied by way of two of said second electrodes and the potential difference measured between two of said first electrodes, or vice versa.

According to another embodiment of the invention, a method of measuring electrical conductivity distribution within a conductive volume includes the steps of positioning adjacent a surface of the body an array of electrodes, with a first group of the electrodes closer to the surface than a second group of the electrodes, applying a stimulation current to selected pairs of electrodes in turn and measuring, for each pair stimulated, corresponding electrical potential differences produced between pairs of the remaining electrodes, and processing the measured potential differences to determine electrical conductivity variations within the body.

According to another aspect of the present invention, an electrode arrangement for an electrical impedance tomography system comprises a plurality of electrodes and support means for supporting the electrodes adjacent a surface of a conductive body the conductivity of which is to be mapped by the system, the arrangement being such that a first group of said plurality of electrodes will be closer to the surface than a second group of the plurality of electrodes.

According to yet another aspect of the invention, an electrode arrangement for an electrical impedance tomography system comprises a plurality of electrodes in an array mounted in a support medium for supporting the electrodes adjacent a surface of a volume to be imaged, the support medium having anisotropic conductivity, its conductivity in a direction that, in use, is normal to the surface, being significantly greater than its conductivity in a transverse direction.

According to a further embodiment of the invention, an electrode arrangement for an electrical impedance tomography system comprises an array of electrodes fixed spatially relative to each other in a rigid support medium, and an interface medium for interfacing the rigid support to a surface of a conductive volume to be measured, the interface medium being conductive so as to connect the electrodes electrically to the surface and pliable so as to conform to variations in relief of the surface.

An advantage of this electrode arrangement of such further aspect, as compared with electrodes which are simply attached directly to the volume, is that the relative position of the electrodes, and the dimensions of the array, are fixed, which facilitates static image reconstruction of the image.

According to yet a further aspect of the invention, an electrode arrangement for use in electrical impedance tomography comprises a plurality of electrode means each formed by a stimulation electrode and a recording electrode closely located spatially. In one embodiment of this aspect, the electrode means comprises an inner electrode surrounded by an outer electrode with an annular channel between them. Electrically insulating sealing means may be provided in the annular channel for contacting said surface, in use, and insulating the inner electrode electrically from the outer electrode.

Various objects, features, aspects and advantages of the present invention will become more apparent from the following detailed description of preferred embodiments of the invention, taken in conjunction with the accompanying drawings.

BEST MODES FOR CARRYING OUT THE INVENTION

Figure 1:
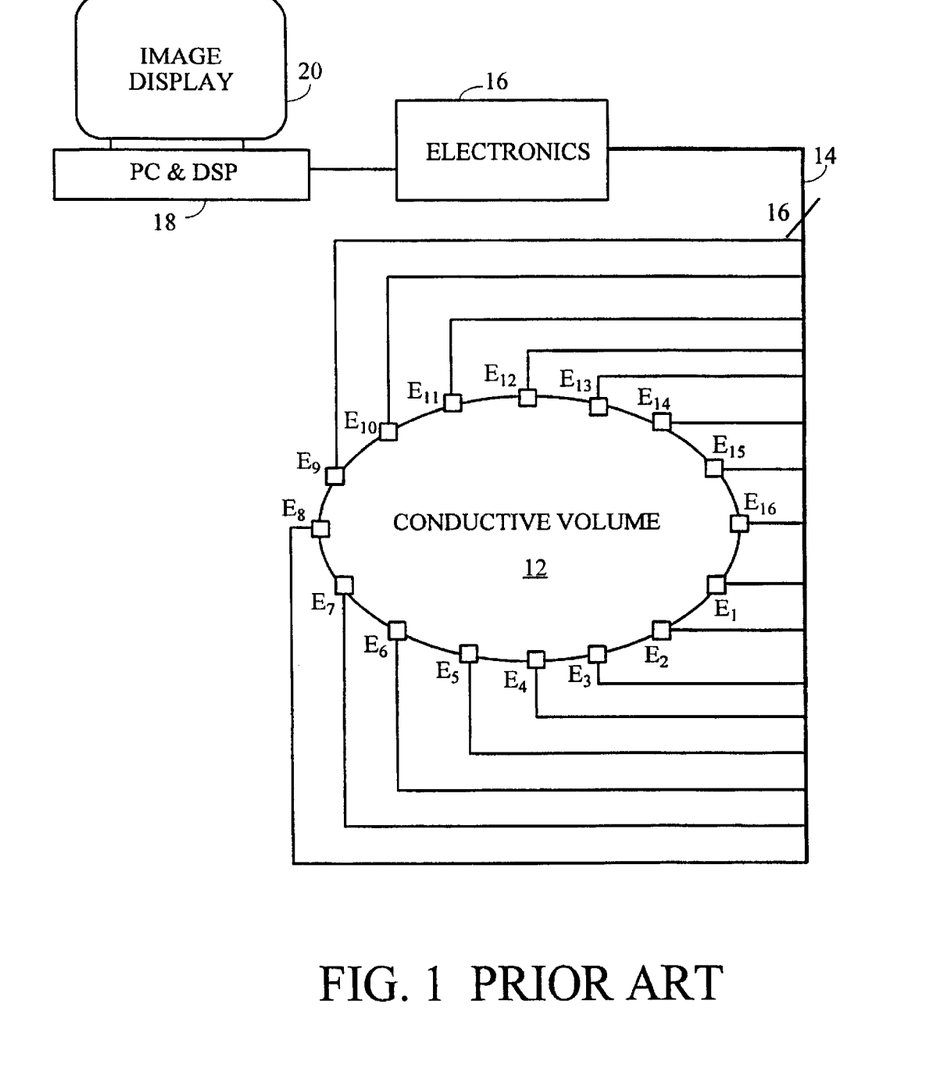
FIG. 1, labelled PRIOR ART, is a diagram of the generic components that are part of a typical EIT apparatus.

Referring to FIG. 1, a typical known EIT apparatus comprises an electrode array comprising sixteen electrodes $E_1$ to $E_{16}$ distributed, equally spaced apart, around a conductive volume 12, to which they are attached directly, if necessary with a suitable conductive gel ensuring good electrical contact. The conductive volume 12 may be, for example, a human thorax. The electrodes are connected by a link 14 to electronic conditioning circuitry 16 which will usually include components such as a current source controlled by a D-to-A-converter, an A-to-D converter, differential amplifier, filter, analog multiplexer, clock, and the digital I/O required to control the circuitry from a computer 18 to which the electronic conditioning circuitry is connected. The computer 18 may be a personal computer equipped with a digital signal processor card used for the image reconstruction process and a suitable display 20 for displaying the images.

Using the procedure disclosed in U.S. Pat. No. 4,617,939, a first pair of the electrodes $E_1$ and $E_2$ are stimulated by injecting a current of, say, 4 mA at 50 kHz, into them and the corresponding potential differences measured between each of the other pairs of electrodes, i.e. ($E_3$–$E_4$), ($E_4$–$E_5$), ($E_5$–$E_6$), and so on up to ($E_{15}$–$E_{16}$). The potential differences between electrodes $E_{16}$ and $E_1$, $E_1$ and $E_2$, and $E_2$ and $E_3$ are not measured because the voltage drop across the contact resistance due to the injected current would affect the measurements.

The next pair of electrodes $E_2$ and $E_3$ then are stimulated and the potential differences between pairs of the other electrodes measured. The procedure is repeated until all of the pairs of electrodes have been stimulated in turn. The accumulated measurements are processed by the computer 18 and an image of the electrical impedance variation across the conductive volume is created and displayed on display unit 20. Various algorithms have been disclosed for computing these impedance variation, such as the so-called "back-projection" reconstruction algorithm and the regularized inverse of the sensitivity matrix.

While this procedure might appear satisfactory theoretically, in practice, noise may obscure many of the readings and reduce the quality of the reconstruction. Embodiments of the present invention favour high signal-to-noise ratio measurements by limiting the measurements, for a given stimulation pair, to that pair or pairs whose "recording" electric field vectors most closely align with the electric field vectors of the stimulated pair of electrodes. It will be appreciated that the recording electrodes measure potential difference so their "recording" electric field vectors is really that which would be produced if a stimulation current were injected into them. Generally, the present invention aims to keep the stimulating and recording electric field vectors as close to each other as possible. (Ideally, they would be superimposed). Various arrangements for doing so will now be described.

A first embodiment of the invention will now be described with reference to FIGS. 2 and 3 in which the electronic conditioning circuitry 16', computer 18' and display unit 20' are similar to those of FIG. 1 and so have the same reference numerals, but with a prime.

Figure 2:
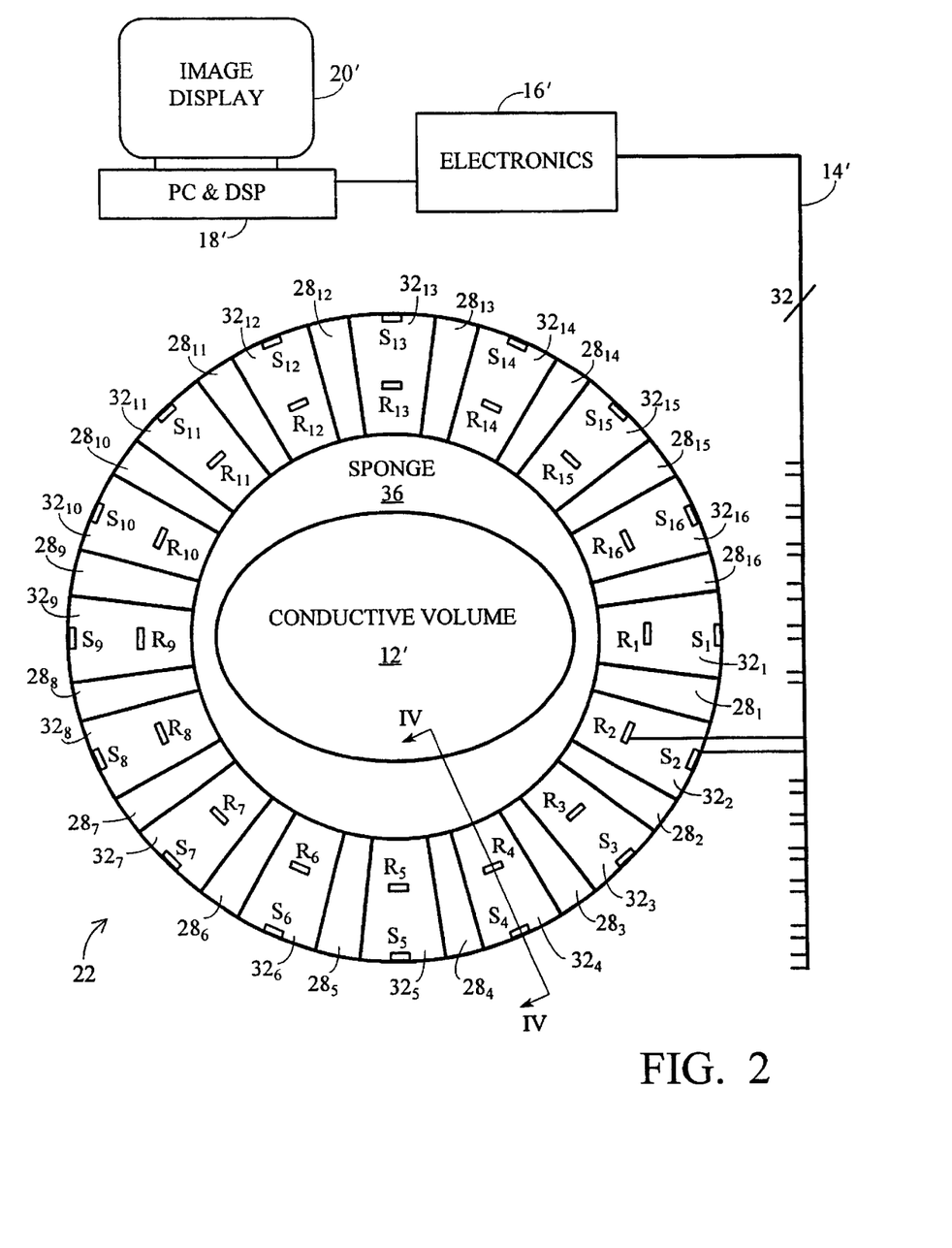
FIG. 2 is a diagram of a first embodiment of the invention comprising an annular EIT electrode array.
Figure 3:
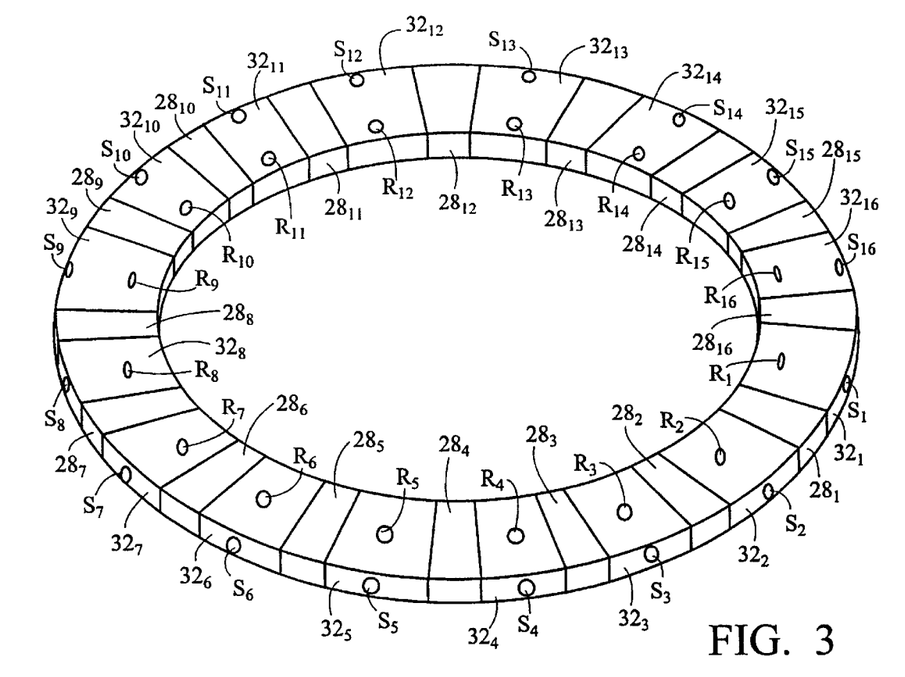
FIG. 3 is a three-dimensional view of the annular electrode array of FIG. 2.
Figure 4:
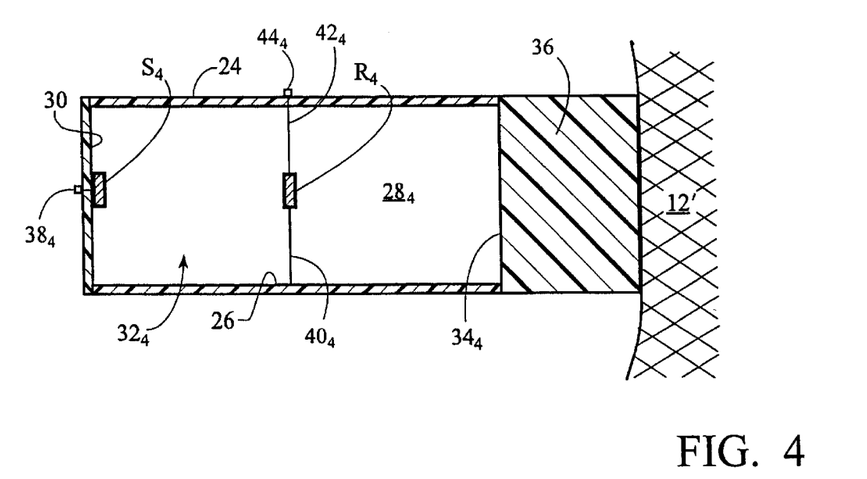
FIG. 4 is a cross-sectional detail view taken on the line IV—IV of FIG. 2.

The electrode array 22 shown in FIGS. 2 and 3 differs from that shown in FIG. 1 in that it comprises two groups of electrodes arranged in an annular configuration, i.e. in two rings, one within the other, and supported by an annular support. The inner group comprises recording electrodes $R_1$ to $R_{16}$ and the outer group comprises stimulating electrodes $S_1$ to $S_{16}$. The annular support comprises annular flanges 24 and 26 (see FIG. 4) bonded to opposite sides of an array of radial separators $28_1$–$28_{16}$ and a circumferential band 30 is bonded to their respective outer edges, forming a ring of wedge-shaped compartments or cells $32_1$ to $32_{16}$ which are open at their inner ends $34_1$ to $34_{16}$ and alternate with separators $28_1$ to $28_{16}$. The annular flanges 24 and 26, separators 28, and outer band 30 are of insulating material. Each pair of an inner electrode R and an outer electrode S mounted in a corresponding one of the plurality of wedge-shaped compartments or cells $32_1$ to $32_{16}$.

The wedge-shaped compartments $32_1$ to $32_{16}$ are equally distributed and each subtends a 15 degree angle. They contain a conductive material whose electrical conductivity is comparable to the expected average electrical conductivity of the imaging medium. For example, for measuring a human body part with a conductivity of, say, 0.002 mho/cm, the compartments $32_1$ to $32_{16}$ might contain agar jelly formed by mixing agar powder with saline solution to form a conductive gel, giving a conductivity for the wedge-shaped compartment of about 0.002 mho/cm. The separators $28_1$ to $28_{16}$ are poorly conductive and each subtends an angle of 7.5 degrees so that the annular support is circular. The separators $28_1$ to $28_{16}$ might be of synthetic plastics material, for example polypropylene.

In use, a conductive interfacing medium 36, for example sponge material soaked in saline solution, is provided between the conductive volume or body 12' and the innermost surface of the annular support 22, i.e. the innermost surface of the agar jelly filling the compartments $32_1$ to $32_{16}$. The sponge 36 is pliable and conforms to the shape of the conductive volume surface. It connects each of the electrodes $R_1$ to $R_{16}$ and $S_1$ to $S_{16}$ electrically to the surface of conductive volume 12'. The conductivity of the interfacing medium 36 is comparable to the conductivity of the imaging medium 12'.

The mounting of the electrodes $S_1$ to $S_{16}$ in compartments $32_1$ to $32_{16}$ is the same in each case, so only the mounting of electrodes $S_4$ and $R_4$ described—as an example. Thus, the stimulation electrode is mounted upon the inner face of band 30 and connected through the band to terminal $38_4$. The recording electrode $R_4$ is suspended in the middle of the compartment $32_4$ by a plastics ligature $40_4$, extending from the annular flange 26 and a conductive filament $42_4$ extending from the other annular flange 24. The filament $42_4$ connects to terminal $44_4$ on the outer surface of flange 24. The terminals $38_1$ to $38_{16}$ and $44_1$ to $44_4$ are not shown in FIGS. 2 and 3 for clarity.

The terminals 38 and 44 are connected to the electronic conditioning circuit 16'. For convenience, the individual connections are not shown in FIGS. 2 and 3. The circuit 16' permits selection of individual pairs of the outer electrodes $S_1$–$S_{16}$ for stimulation by a suitable current of, say, 0.1–1 mA at 10–100 kHz, and selection of pairs of the inner electrodes $R_1$–$R_{16}$ for measurement of potential differences across them. Each of the electrodes $R_1$ to $R_{16}$ and $S_1$ to $S_{16}$ comprises a disc mounted with its plane normal to a radius of the annular support, each pair of electrodes in a cell being aligned radially, i.e. on a line extending normal to the surface of the body 12'. Each electrode is about 6 mm in diameter. The electrodes $R_1$ to $R_{16}$ and $S_1$ to $S_{16}$ in their respective compartments are spaced apart radially by a distance sufficient to reduce/avoid shielding effects. Other sizes of electrodes, for example from 2 mm to 10 mm diameter, are available. If they were used, the spacing would be adjusted appropriately.

In view of the alternating "high" conductivity of compartments $32_1$ to $32_{16}$ and "low" conductivity of separators $28_1$ to $28_{16}$, the annular support can be considered to have anisotropic conductivity, i.e. high conductivity for currents flowing radially from an electrode S towards the volume 12' and low conductivity for currents flowing circumferentially from one compartment towards its neighbour.

The manner in which this arrangement of electrode geometry and media favours the enhancement of the sensitivity of the apparatus will now be described.

Figure 5:
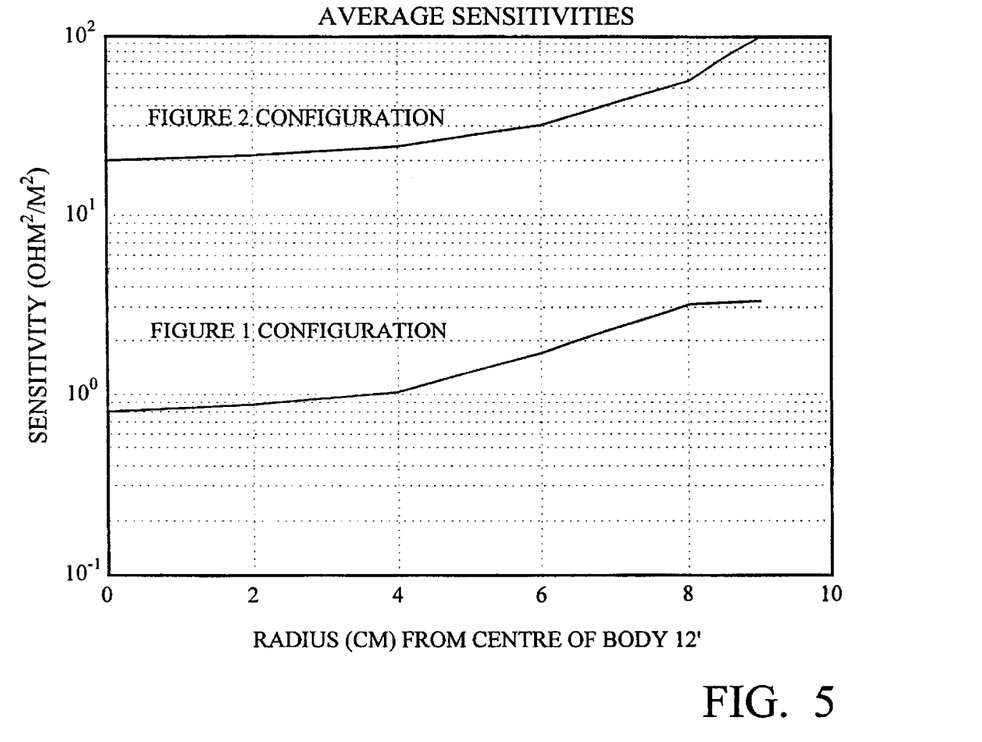
FIG. 5 compares the sensitivity values of the annular EIT electrode array of FIG. 2 with those of the EIT system of FIG. 1, for radial positions.

FIG. 5 illustrates the average sensitivity, in the radial direction, obtained using a finite element model, for an electrical impedance tomography apparatus using the annular electrode array of FIG. 2, and that for an equivalent conventional electrical impedance tomography apparatus using the electrode array of FIG. 1. In both cases the conductive volume 12' has a radius of 10 cm, with a uniform conductivity. For proof of concept, the annulus in FIG. 2 extends from 10 cm to 15 cm and has a conductivity 10 times larger than the conductivity of conductive volume 12'. The medium separating the individual compartments, i.e. of separators $28_1$ to $28_{12}$, is set to a conductivity value of 1% of the conductivity of conductivity volume 12'.

The average sensitivity curve obtained for the conventional electrode array of FIG. 1 uses configurations of stimulator and recording electrode pairs as disclosed by Brown et al. in U.S. Pat. Nos. No. 4,617,939. As mentioned earlier, in this approach, a pair of neighbouring electrodes is used to stimulate while the electrical potential is measured with the remaining pairs of electrodes. The process is repeated until all the independent combinations are exhausted. The electrodes used for stimulation, however, are not used also for measurement.

The average sensitivity curve for the electrode configuration shown in FIG. 2 is obtained using pairs of electrodes in the outer group $S_1$–$S_{16}$ to apply stimulation current and the corresponding pairs of electrode in the inner group $R_1$–$R_{16}$ to measure the resulting electrical potential.

The resolution of the reconstructed image depends upon the sensitivity of the apparatus to changes of the electric conductivity in the conductive volume 12'. The sensitivities depicted in FIG. 5 were obtained using the sensitivity expression described by D. B. Geselowitz in "An Application of Electrocardiographic Lead Theory to Impedance Plethysmography", IEEE Trans. Biomed. Eng., Vol. BME-18, pp. 38–41, January 1971, and by J. Lehr in "A Vector Derivation Useful in Impedance Plethysmographic field calculation", IEEE Trans. Biomed. Eng., Vol. BME-19, pp. 156–157, March 1972.

Figure 6:
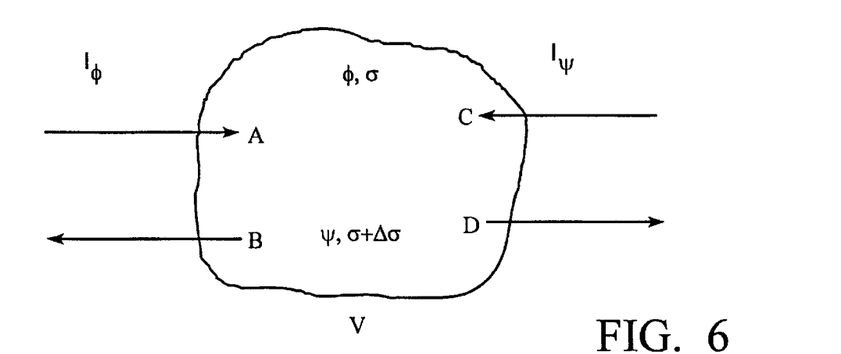
FIG. 6 illustrates the sensitivity theorem used in determining electrical impedance tomography (EIT) of a volume conductor.

The theoretical basis for the reconstruction algorithm employed by embodiments of the invention will be described with reference to FIG. 6. When the conductivity distribution changes from $\sigma(x,y,z)$ to $\sigma(x,y,z)+\Delta\sigma(x,y,z)$, the change in the transfer impedance $\Delta Z$ for the pair of stimulating electrodes (A,B) and recording electrodes (C,D) can be given as:

$$\Delta Z = -\int \Delta\sigma \frac{\vec{\nabla}\phi(\sigma)}{I_\phi} \cdot \frac{\vec{\nabla}\psi(\sigma + \Delta\sigma)}{I_\psi} dv \quad (1)$$

where:
- $\Phi$ is the potential distribution when the current $I_\Phi$ is applied to the electrode pair (A,B).
- $\Psi$ is the potential distribution when the current $I_\Psi$ is applied to the electrode pair (C,D).
- $\sigma(x,y,z)$ is the conductivity distribution when $\Psi$ is established for $I_\Psi$.
- $\sigma(x,y,z)+\Delta\sigma(x,y,z)$ is the conductivity distribution when $\Psi$ is established for $I_\Psi$.

The term $\vec{\Delta}\psi(\sigma+\Delta\sigma)$ in expression (1) can be expanded with respect to $\Delta\sigma$. Assuming small $\Delta\sigma$'s, the higher order terms can be neglected and expression (1) is expressed as follows:

$$\Delta Z = -\int \Delta\sigma \frac{\vec{\nabla}\phi(\sigma)}{I_\Phi} \cdot \frac{\vec{\nabla}\psi(\sigma)}{I_\psi} dv \quad (2)$$

Since the term $\Delta Z$, the difference between the measured transfer impedance and the assumed transfer impedance, is known, the difference in the conductivity distribution $\Delta\sigma$ can be obtained. Dividing the region of interest into small domains over which the conductivity is assumed constant enables expression (2) to be discretized and expressed as the following matrix equation:

$$\Delta Z_i = \sum_{j=1}^{m} S_{ij}\Delta\sigma_j \quad (3)$$

where:
- $\Delta Z_i$ is the difference in transfer impedance for the ith combination of a pair of stimulating electrodes and a pair of recording electrodes;
- $\Delta\sigma_j$ is the unknown conductivity difference for the region element j;
- $S_{ij}$ is the sensitivity coefficient term for the stimulating/recording electrode pair combination i, at the element j; and
- m is the number of domains into which the region has been divided.

The term $S_{ij}$ is given as follows:

$$S_{ij} = -\int_{v_j}\left(\frac{\vec{\nabla}\Phi \cdot \vec{\nabla}\Psi}{I_\Phi I_\Psi}\right)dv_j \quad (4)$$

An examination of expression (4) indicates that the sensitivity term can be enhanced by an apparatus that could maximize the integrand. Sensitivity enhancement is achieved by selecting configurations of stimulating and recording electrode pairs that favour the scalar product in the numerator and using an annulus medium with an anisotropic conductivity that limits the current intensities at the denominator.

Electrode configurations. The annular electrode array of FIG. 2 allows electrode configurations that can maximize scalar products of stimulating and recording electric field vectors more so than could be obtained with the electrodes of FIG. 1. It permits more combinations of electrodes to be made, with a greater number of different geometries.

It should be appreciated that the stimulating electrodes need not be diametrically opposite each other. Referring to FIG. 2, using pairs of electrodes in the outer group $S_1$ to $S_{16}$ to stimulate the body and pairs of electrodes in the inner group $R_1$ to $R_{16}$ to measure the resulting electrical potentials tends to maximize the scalar product in the numerator of expression (4).

Annulus conductivity. The sensitivity of the apparatus to a change in the electrical conductivity at a position (x,y) in the conductive volume is an inverse function of the product of the total electric current intensities that would be required to produce the electric field intensity of the stimulating and recording electrode pairs at position (x,y). Disposing the electrodes in sectors whose boundaries are poorly conductive, produces an annulus medium with an anisotropic conductivity, vis. conductive in the radial direction and poorly conductive in the direction. This arrangement forces the current to flow in the medium of interest, i.e. the conductive volume, as opposed to the extended medium. It favours a larger ratio of the electric field to current intensity, in the medium of interest.

The sensitivity function used to determine the average sensitivities represented in FIG. 5 was not optimized for the various parameters that define the annulus. Key parameters are expected to be the following:

A. Annulus dimension: The size of the annulus used for this evaluation has an outer to inner radius ratio of 1.5. Evaluations have shown that as the ratio increases, and the electrodes are set further away from the imaging volume, the sensitivity decreases. Conversely, as the ratio decreases, and the electrodes get closer to the imaging medium and the sensitivity increases. Although this is true for a discrete point electrode model, the optimal practical ratio will be determined by the size of the electrodes and the minimum separation required to avoid mutual shielding.

B. Annulus electrical conductivity: Enhanced sensitivity is obtained when the annulus is configured with an anisotropic electrical conductivity distribution, that is, a large ratio of the radial to the azimuthal electrical conductivity. No significant improvement was gained by decreasing the azimuthal electrical conductivity below 1% of the average imaging medium electric conductivity.

C. Electrodes: A minimum of 32 electrodes were considered, arranged in two concentric rings. For this evaluation, each wedge-shaped compartment held two electrodes, aligned along the diameter. One electrode was positioned at the edge of the annulus and the other was positioned at the centre of the annulus. Although this was effective for the model, in practice, of course, the other electrode cannot be any closer to the centre than the inner surface of the annulus. It is expected that standard commercial AgCl disk shaped electrodes would be used for this application.

Measurement procedure. As stated earlier, it is desirable to maximize the scalar product of the electric field vectors for the stimulating pair of electrodes and the "recording" electric field vectors for the recording pair of electrodes. Consequently, for a given pair of stimulating electrodes, it is sufficient to measure the potential difference between that pair or pairs of electrodes which are closest spatially to the stimulating electrodes and not to measure the potential differences between other pairs of electrodes. This measurement procedure will now be described with reference to the flowchart of FIG. 7. In order to illustrate the stimulation/measurement strategy explicitly, an example will be given using the geometry depicted in FIG. 2. The outer electrode set ($S_1$–$S_{16}$) are used as stimulating electrodes and the inner electrode set ($R_1$–$R_{16}$) as recording electrodes. It should be appreciated that the outer set could be replaced with a set on the inner surface, as per the comments above.

Figure 7:
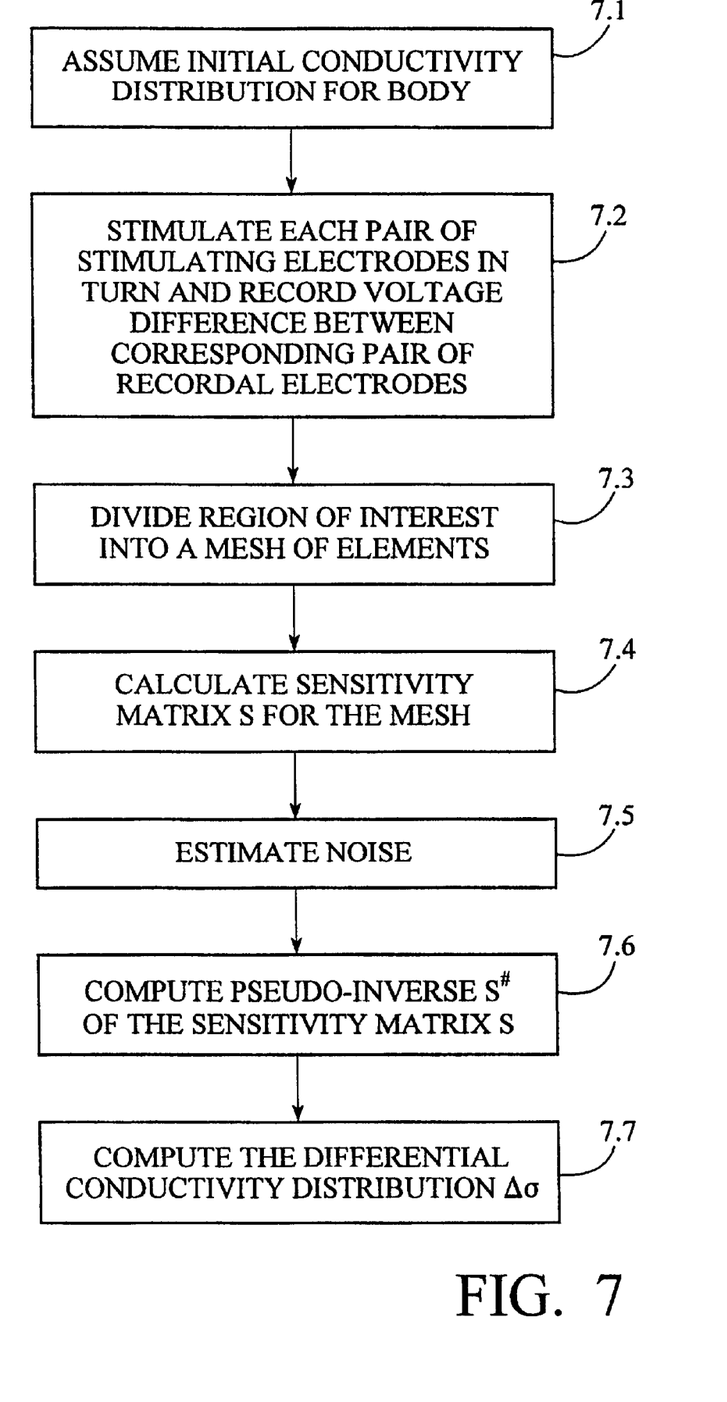
FIG. 7 is a flowchart representing a typical measurement procedure using the electrode means of FIG. 2.

Following positioning of the electrodes $S_1$–$S_{16}$ and $R_1$–$R_{16}$ upon the conductive volume to be imaged, an initial conductivity distribution appropriate to the volume would be assumed (step 7.1). In the absence of other information from, say, previous measurements of the same or similar volumes, a uniform mean conductivity distribution would be assumed. For example, for landmine detection, this might be a typical conductivity distribution of the particular type of soil whereas, for human body imaging, it might be a typical conductivity distribution for that part of the human body.

In step 7.2, a series of measurements are made, passing a known current through each pair of stimulation electrodes $S_1$ to $S_{16}$ in turn and recording the potential difference across the "closest" pair of electrodes, i.e. having the recording electric field vectors most closely aligned with those of the stimulating pair of electrodes. For example, when stimulating $S_1$ and $S_2$, the potential difference between $R_1$ and $R_2$ only would be measured.

The stimulation/recording pairings proposed here are:

TABLE 1

Stimulate/Measure Configuration

| Stimulation Pair | Recording Pair | Pair Gap |
|---|---|---|
| $S_1,S_2$ | $R_1,R_2$ | 1 |
| $S_2,S_3$ | $R_2,R_3$ | 1 |
| $S_3,S_4$ | $R_3,R_4$ | 1 |
| ... | ... | ... |
| $S_1,S_3$ | $R1,R_3$ | 2 |
| $S_2,S_4$ | $R_2,R_4$ | 2 |
| ... | ... | ... |
| $S_1,S_4$ | $R_1,R_4$ | 3 |
| ... | ... | ... |

This pattern yields 120 independent combinations for 16 compound electrodes (stimulate-record pairs). It should be noted that the stimulating electrodes and the recording electrodes are always identically numbered, and hence closely located. Other stimulation/recording electrode configurations which share this feature will have some benefit. An example of such an alternative, possible with only a single set of electrodes as shown in FIG. 1 (denoted $E_1, E_2 \ldots E_{16}$) is:

TABLE 2

Alternative Stimulate/Record Configuration

| Stimulation Pair | Recording Pair | Pair Gap |
|---|---|---|
| $E_1,E_3$ | $E_2,E_4$ | 2 |
| $E_2,E_4$ | $E_3,E_5$ | 2 |
| $E_3,E_5$ | $E_4,E_6$ | 2 |
| ... | ... | ... |
| $E_1,E_4$ | $E_2,E_5$ | 3 |
| $E_2,E_5$ | $E_3,E_6$ | 3 |
| ... | ... | ... |

This pattern has a reduced number of independent combinations, since it starts with a stimulating electrode gap of 2, for example, but will show some of the benefit of the proposed configuration, and is shown as a simple example of an alternative manifestation of the stimulate/record configuration described herein.

Referring again to the flowchart of FIG. 7, once the measurements have been made, in step 7.3, the region of interest, i.e. the region in which current might flow, is divided into a mesh of elements. In FIG. 2, the region of interest is the conductive volume 12', the sponge 36 and the annular array of compartments $32_1$–$32_{16}$. Each element has dimensions equal to approximately 10 per cent of the spacing between each pair of the recording electrodes $R_1$ to $R_{16}$. The mesh could be triangular or rectangular, as desired, and the region could be two-dimensional or three-dimensional.

In step 7.4, the sensitivity matrix $S_{ij}$ is calculated for the mesh using the electrode geometry, initial conductivity distribution, and applied currents, according to equation [4], for the region of interest.

In step 7.5, an estimate is made of the noise present in the potential difference measurements divided by the applied stimulation current. This scaled noise value is used to determine a parameter $\mu$ which is the ratio of the scaled noise value to the root mean square (RMS) of the initial conductivity distribution.

In step 7.6, the pseudo-inverse $S^{\#}_{ij}$ of the sensitivity matrix $S_{ij}$ is calculated according to equations (5) and (6).

In step 7.7, the differential conductivity distribution $\Delta\sigma$ is calculated according to equation (7).

Preferred Electrode Configuration and Compound Electrodes.

Compound electrodes are so named because they comprise two parts, one part being used for stimulation and the other for recording. It has been found that compound electrodes, in conjunction with the novel measurement procedure described above, provide significantly better performance in physically realistic (noisy) situations. Analysis has shown that this improvement in performance is due both to sensitivity amplitude enhancements (due to alignment of the electric field stimulating and recording electric field vectors) and a better representation (more suitable for reconstruction) of the set of measurements possible by the proposed recording configuration.

Figure 8:
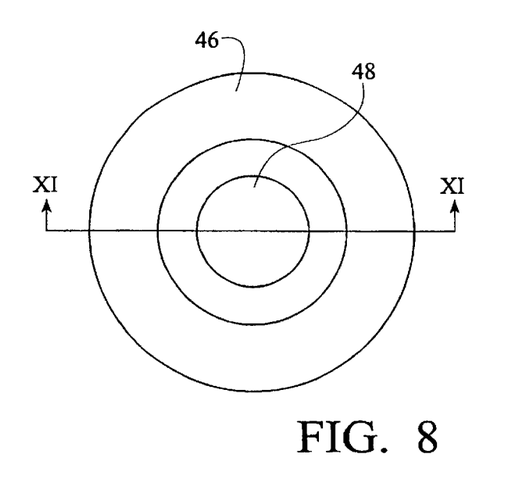
FIG. 8 is a plan view of an alternative form of electrode means, comprising an inner electrode and an outer electrode (also referred to as a compound electrode.
Figure 9:
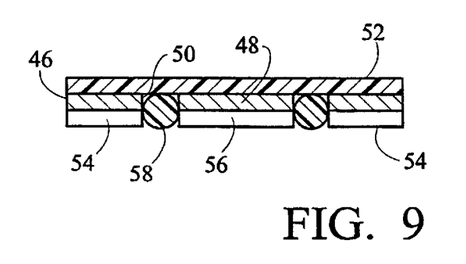
FIG. 9 is a cross-sectional view of the electrode means of FIG. 8.

A potential problem associated with compound electrodes is the possibility of a partial electrical short circuit between the stimulating and measuring electrode, due to the close proximity of these electrodes. Simulations have indicated that satisfaction will be obtained with spacing of the component electrodes of a compound electrode such as to render the voltage associated with this extra (surface) current path approximately 0.1% of that associated with the conventional path (through the region of interest). For a human body this requirement translates into a resistance of (for skin surface alone) approximately 5 MΩ. An example of a suitable compound electrode is shown in FIGS. 8 and 9. The compound electrode comprises an annular outer electrode 46 surrounding a circular inner electrode 48 with an annular slot 50 between them. The electrodes 46 and 48 are bonded to an insulating planar support 52 and their exposed surfaces are coated with layers of conductive gel 54 and 56, respectively. An "O" ring 58 of insulating material is located in the annular slot 50. The diameter of the "O" ring 58 is approximately equal to the depth of the annular slot 50 so that, when the compound electrode is applied to the surface of the volume under investigation, the "O" ring 58 will prevent gel 54/56 from exuding across the annular slot 50 and causing, effectively, a short-circuit between the inner and outer electrodes. In use, a plurality of such compound electrodes would be distributed about the surface of the body being investigated. Current could be applied to the respective outer electrodes of a pair of compound electrodes and the potential difference recorded between the inner electrodes of the same pair. Conversely, the inner electrodes could be stimulated and the potential difference recorded between the outer electrodes.

It should be appreciated that other configurations of compound electrode could be used. For example, either or both of the electrodes could be rectangular. It is also envisaged that each compound electrode might comprise an array or grid of stimulation electrodes interspersed with an array or grid of recording electrodes.

Figure 10:
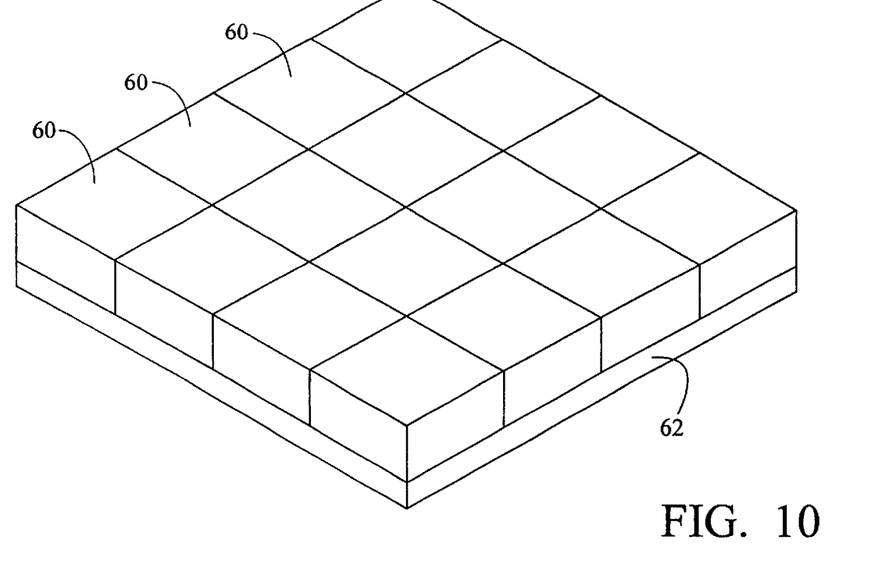
FIG. 10 illustrates a second embodiment of the invention in the form of a planar rectangular electrode array for a ground probing application.
Figure 11:
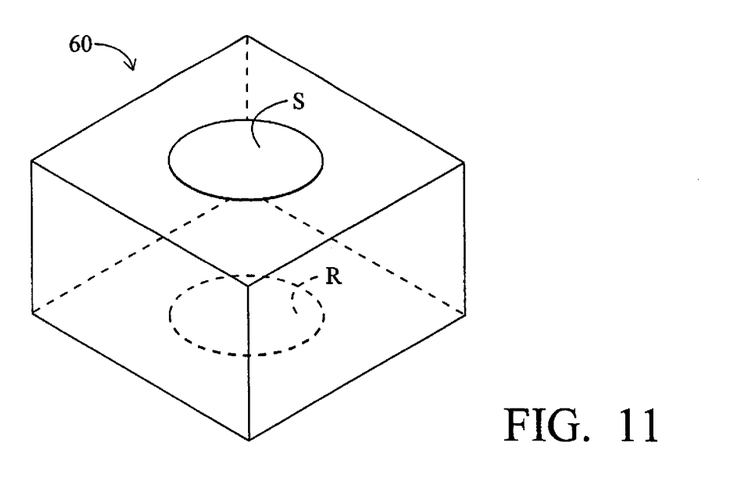
FIG. 11 illustrates one cell of the electrode array of FIG. 10.

The annular electrode array of FIGS. 2 and 3, whether with the individual electrodes or with the compound electrodes, is well suited for medical diagnostics applications applied to a patient's head, limb or torso. Nevertheless, the enhanced sensitivity approach illustrated with the annular geometry can also be applied to other electrode configurations. Thus, FIG. 10 illustrates a two-dimensional array of electrode cells which is shown as rectangular but could have other shapes. This electrode array is envisaged for ground imaging applications, such as landmine detection. The array comprises juxtaposed individual electrode cell units 60. As shown in FIG. 11, each cell comprises a pair of electrodes R, S immersed in a conductive material, for example a jelly formed from agar and saline solution, as before.

The cell units 60 lie on a bed 62 (FIG. 10) of conductive material that provides the electrical interface with the ground. This bed 62 would have insulating partitions (not shown) to maintain anisotropic conductivity.

Figure 12:
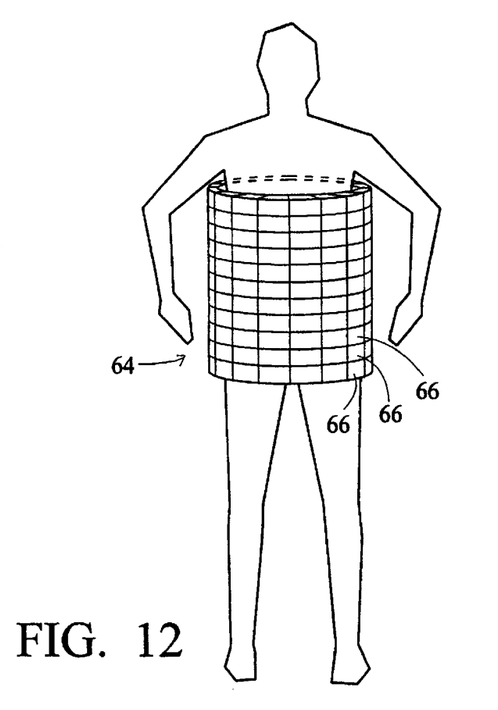
FIG. 12 illustrates a third embodiment in the form of a cylindrical electrode array for three-dimensional imaging of a human torso.

FIG. 12 illustrates another possible embodiment, where a flexible vest 64 comprises similar individual electrode cells 66 forming a cylindrical array which, as shown, can be wrapped around a human torso and used for three-dimensional imaging. It will be appreciated that other geometries are also feasible, such as a special cap for head imaging applications or a special brassiere for breast imaging applications.

It should be appreciated that, if the radially-spaced electrodes S/R of FIGS. 2–4 and 10–12 were replaced by compound electrodes, the agar-filled compartments or cells would not be required, since the compound electrodes could lie flat upon the surface. However, it is envisaged that, to facilitate calculations, the compound electrodes would still be in a rigid support, if necessary, with an intervening sponge 36, or the like.

Reconstruction Technique

The proposed reconstruction technique is based on the construction of a probabilistically regulated, pseudo inverse of the sensitivity matrix introduced above and mentioned in step 7.4. The construction of this pseudo inverse is very straightforward, and follows the following steps:

Calculate the singular value decomposition of the sensitivity matrix.

$$S = U \Lambda V^T \qquad (5)$$

Replace each singular value $\lambda_i$ in $\Lambda = \text{diag}(\lambda_i)$ with $\lambda_i^{\#} = \lambda_i/(\lambda_i^2 + \mu^2)$, producing $\Lambda^{\#} = \text{diag}(\lambda_i^{\#})$. The parameter $\mu$ is the ratio of the noise in the measured potential differences to the root mean square (RMS) of the conductivity distribution. Thus, in this sense it is the inverse of the SNR.

Form the pseudo inverse $$S^{\#} = V \Lambda^{\#} U^T \qquad (6)$$

which can be used to compute conductivity perturbations from potential difference recordings, i.e. reconstruct the EIT image, since $$\Delta \sigma_i = \sum_{j=1}^{n} S_{ij}^{\#} \Delta Z_j, \qquad (7)$$

where n is the number of independent measurements taken,

This approach has been found to respect the inherent low pass filtering of the EIT process, and offers a rapid and robust option for EIT image reconstruction.

Figures 13A, 13B, 13C:
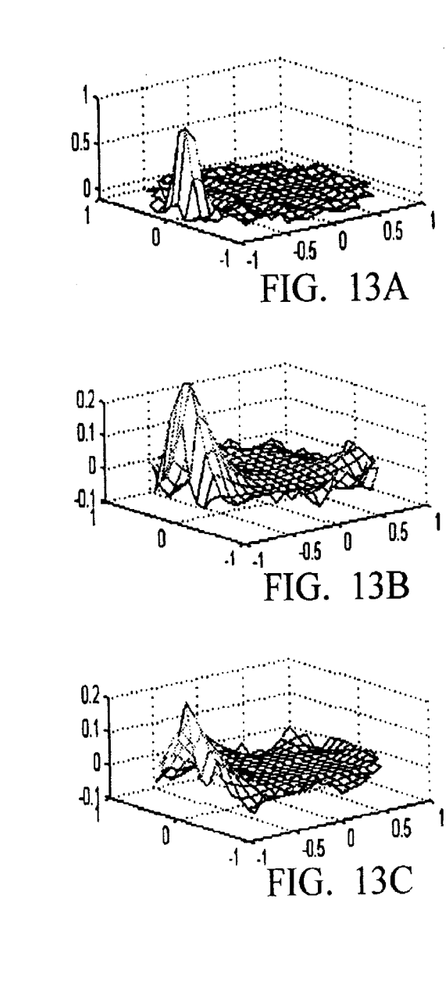
FIGS. 13A to 13I illustrate the image reconstruction obtained from a conventional EIT electrode array, such as that shown in FIG. 1, and an electrode array in which the stimulating electrodes and recording electrodes are co-located, such as that shown in FIG. 2.
Figures 13D, 13E, 13F:
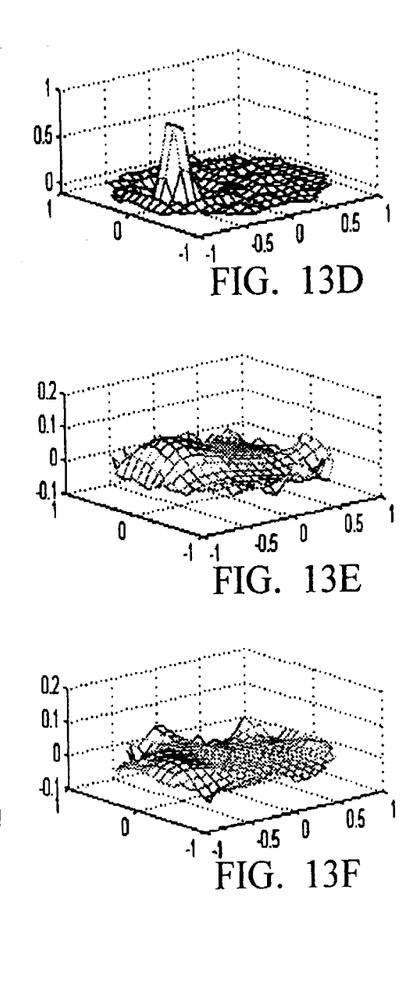
Figures 13G, 13H, 13I:
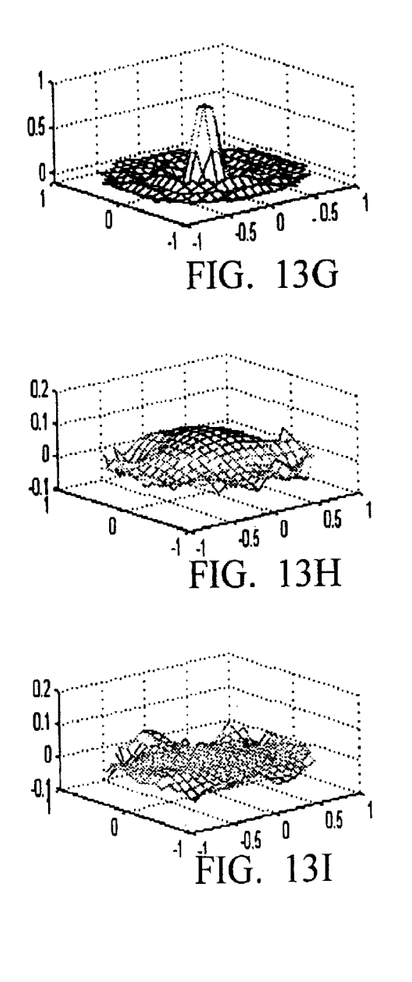

FIGS. 13A to 13I illustrate a comparison between the novel measurement procedure set out in Table 1, using compound electrodes as per FIG. 8, and the measurement procedure disclosed by Brown at al. in U.S. Pat. No. 4,617,939, but in both cases using the reconstruction technique described above. FIGS. 13A to 13I depict the reconstruction of a perturbation covering approximately 10% of the diameter of a circular region of interest at three different locations. As shown in FIGS. 13A, 13D and 13G, with zero noise, both Brown et al.'s procedure and the procedure of the present invention reproduce the perturbation very accurately. Thus, FIG. 13A shows a maximum a posteriori (MAP) estimate of a perturbation near the circumference of the region. FIG. 13B shows the (MAP) estimate of the differential conductivity distribution $\Delta \sigma$ for a circular array of 16 compound electrodes of the kind shown in FIG. 8. FIG. 13C shows the corresponding MAP estimate for the conventional electrode configuration fo FIG. 1 using Brown et al.'s measurement technique.

FIGS. 13D to 13F correspond to FIGS. 13A to 13C fo a perturbation which is closer to the middle of the rigion and FIGS. 13G to 13I are the corresponding reconstructions for a perturbation at the centre of the region.

The present invention embraces various modification and substitutions. For example, the electrodes could be in a fixed array and a separate current generator provided for cach pair stimulated. Alternatively, a single current generator could be used to stimulate cach pair of electrodes in turn, using a commutation switching circuit, enabling a more expensive current generator to be used.

It is also envisaged that only two stimulating electrodes and two recording electrodes could be used. The various locations would br predefined and the electrodes repositioned at selected locations in turn until all lacations had been stimulated as required.

It is envisaged that, instead of providing a personal computer with a DSP card for performing the reconstruction, a suitable custom integrated circuit, preprogrammed with the reconstruction algorithm software, could be combined with the electronic conditioning circuitry in an interface which would connect to a conventional personal computer and/or even directly to a display device.

INDUSTRIAL APPLICABILITY

The compound electrode arrangement may be easier to manufacture. The measurement procedure facilitates simpler implementations for a given sensitivity.

What is claimed is:

1. A method of determining electrical impedance tomography of a conductive volume (12) comprising the steps of selecting, in turn, each of a plurality of pairs of locations (S) upon a surface of the volume (12) and supplying a stimulation current to the surface by way of the selected pair of locations, and recording, for each selected pair, a resulting potential difference between at least one pair (R) of the remaining locations, and processing the recorded potential differences to plot electrical conductivity distribution within said volume, and, for a particular pair of locations stimulated, selecting from among the remaining locations, for recordal, the pair or pairs of locations which, if stimulated, would produce an electric field with vectors most closely aligned with the corresponding vectors of the electric field produced by stimulation of said particular pair of locations, and recording said potential difference at the said pair or pairs of locations so selected for recordal.

2. A method of determining electrical impedance tomography according to claim 1, using a plurality of electrodes ($S_1$–$S_{16}$, $R_1$–$R_{16}$) disposed upon or adjacent said surface each at a respective one of said plurality of locations, comprising the steps of;
   (i) applying a stimulation current to said volume by way of a first ($S_1$) and a second ($S_2$) of said plurality of electrodes at corresponding first and second locations;
   (ii) simultaneously recording the resulting potential difference between that pair ($R_1$, $R_2$) of the remaining electrodes at said pair of locations which, if stimulated, would produce electric field vectors most closely aligned with the electric field vectors produced by stimulation of said particular pair of locations;
   (iii) applying a stimulation current to said body by way of two electrodes ($S_2$, $S_3$) at least one of which was not stimulated in a previous step;
   (iv) simultaneously recording the resulting potential difference between that pair ($R_2$, $R_3$) of the remaining electrodes at said locations which, if stimulated, would produce an electric field with vectors most closely aligned with the corresponding vectors of the electric field produced by the stimulation current applied in step (iii).

3. A method according to claim 2, wherein stimulation current is applied to a said first and second of said plurality of electrodes with no intervening electrodes.

4. A method according to claim 2, wherein said stimulation current is applied to a said first and second of said plurality of electrodes that are spaced apart with one or more other electrodes therebetween.

5. A method according to claim 4, wherein each performance of steps (iii) and (iv) applies said stimulation current to a pair of electrodes that are spaced apart with a different number of intervening electrodes therebetween.

6. A method according to claim 2, wherein, in said steps (i) and (ii), said stimulation current is applied to a said first and second of said electrodes that have no electrodes therebetween, and said potential difference recorded, and, in said steps (iii) and (iv), a stimulation current is applied to a said two electrodes that have one or more electrodes therebetween, and the resulting potential difference recorded.

7. A method according to claim 2, wherein the stimulating currents are applied to selected pairs of a first group ($S_1$–$S_{16}$) of the plurality of electrodes and the resulting potential differences are recorded at selected pairs of a second group ($R_1$–$R_{16}$) of the plurality of electrodes, the electrodes ($R_1$–$R_{16}$) of one of the groups are closer to the surface than the electrodes ($S_1$–$S_{16}$) of the other of the groups.

8. A method according to claim 7, wherein each electrode of the first group is substantially aligned with a corresponding electrode of the second group in a direction extending substantially normal to said surface and said potential difference is recorded between that pair of said electrodes which are aligned with the pair of electrodes to which the stimulation current is applied.

9. A method according to claim 2, wherein each electrode means comprises a stimulation electrode (46) and a recording electrode (48) closely located to each other and both the same distance from said surface, the step of applying stimulation current applies the stimulation current to the stimulation electrodes (46) of two electrode means, respectively, and the corresponding potential difference is measured between the recording electrodes (48) of the same two electrode means.

10. A method according to claim 9, wherein one of the stimulating electrode (46) and the recording electrode (48) surrounds the other.

11. An electrode arrangement for an electrical impedance tomography system comprising a first group of electrodes ($R_1$–$R_{16}$) and a second group of electrodes ($S_1$–$S_{16}$) and support means (24,26,28,30) for supporting the electrodes adjacent a surface of a volume (12') the electrical impedance of which is to be mapped by the system, wherein the first group of electrodes ($R_1$–$R_{16}$) is closer than the second group of electrodes ($S_1$–$S_{16}$) to a part of the support means which, in use, will be adjacent said surface.

12. An electrode arrangement according to claim 11, each electrode of the first group ($R_1$–$R_{16}$) is substantially aligned with an adjacent electrode of the second group ($S_1$–$S_{16}$) in a direction extending substantially normal, in use, to said surface.

13. An electrode arrangement according to claim 12, wherein the support means (24,26,28,30) comprises an annular structure, the first group of electrodes ($R_1$–$R_{16}$) and the second group of electrodes ($S_1$–$S_{16}$) being arranged in an inner ring and an outer ring, respectively, about a central part of the annular structure.

14. An electrode arrangement according to claim 13, wherein the annular structure (24,26,28,30) is circular and the spacing between the inner ring of electrodes and the outer ring of electrodes is about one quarter of the diameter of the inner ring.

15. An electrode arrangement according to claim 11, wherein the support means (24,26,28,30) comprises an annular structure, the first group of electrodes ($R_1$–$R_{16}$) and the second group of electrodes ($S_1$–$S_{16}$) being arranged in an inner ring and an outer ring, respectively, about a central part of the annular structure.

16. An electrode arrangement according to claim 15, the annular structure (24,26,28,30) is circular and the spacing between the inner ring of electrodes and the outer ring of electrodes is about one quarter of the diameter of the inner ring.

17. An electrode arrangement according to claim 11, wherein the support means comprises a plurality of compartments ($32_1$–$32_{16}$), each comprising a conductive medium for contacting the surface of a volume (12') to be imaged, and lower conductivity partitions ($28_1$–$28_{16}$) between adjacent compartments, each compartment housing a pair of electrodes comprising one electrode from said first group ($S_1$–$S_{16}$) and one electrode from said second group ($R_1$–$R_{16}$).

18. An electrode arrangement according to claim 17, wherein the electrodes are supported in a planar array (60,62), and each electrode of said first group is spaced from an associated electrode of said second group in a direction substantially perpendicular to the plane of the array.

19. An electrode arrangement according to claim 11, wherein the support means (24,26,28,30) is rigid and a conductive interface medium (36) is disposed for juxtaposing between an inner surface of said support means and the surface of the volume (12) to be measured, the interface medium comprising a material that is conformable to contour variations of said surface of the volume.

20. An electrode arrangement according to claim 19, wherein the interface medium material (36) has a conductivity comparable to that of the volume to be measured.

21. An electrode arrangement according to claim 19, wherein each electrode of the first group ($R_1$–$R_{16}$) is substantially aligned with an adjacent electrode of the second group ($S_1$–$S_{16}$) in a direction extending substantially normal, in use, to said surface.

22. An electrode arrangement according to claim 19, wherein the support means (24,26,28,30) comprises an annular structure, the first group of electrodes ($R_1$–$R_{16}$) and the second group of electrodes ($S_1$–$S_{16}$) being arranged in an inner ring and an outer ring, respectively, about a central part of the annular structure.

23. An electrode arrangement according to claim 22, wherein the annular structure (24,26,28,30) is circular and the spacing between the inner ring of electrodes and the outer ring of electrodes is about one quarter of the diameter of the inner ring.

24. An electrode arrangement according to claim 19, wherein the support means comprises a plurality of compartments ($32_1$–$32_{16}$), each comprising a conductive medium for contacting the surface of a volume (12') to be imaged, and lower conductivity partitions ($28_1$–$28_{16}$) between adjacent compartments, each compartment housing a pair of electrodes comprising one electrode from said first group ($S_1$–$S_{16}$) and one electrode from said second group ($R_1$–$R_{16}$).

25. An electrode arrangement according to claim 24, wherein the interface medium material (36) has a conductivity comparable to that of the volume to be measured.

26. An electrode arrangement according to claim 19, wherein the electrodes are supported in a planar array (60,62), and each electrode of said first group is spaced from an associated electrode of said second group in a direction substantially perpendicular to the plane of the array.

27. An electrode arrangement according to claim 11, wherein the support means (24,26,28,30) has anisotropic conductivity with its conductivity in said direction normal to said surface, in use, being significantly higher than its conductivity in directions transverse thereto.

28. An electrode arrangement according to claim 27, wherein the support means (24,26,28,30) comprises a plurality of higher conductivity sectors (32) alternating with, and defined by, a plurality of lower conductivity regions (28).

29. An electrode arrangement according to claim 27, wherein each electrode of the first group ($R_1$–$R_{16}$) is substantially aligned with an adjacent electrode of the second group ($S_1$–$S_{16}$) in a direction extending substantially normal, in use, to said surface.

30. An electrode arrangement according to claim 27, wherein the support means (24,26,28,30) comprises an annular structure, the first group of electrodes ($R_1$–$R_{16}$) and the second group of electrodes ($S_1$–$S_{16}$) being arranged in an inner ring and an outer ring, respectively, about a central part of the annular structure.

31. An electrode arrangement according to claim 30, wherein the annular structure (24,26,28,30) is circular and the spacing between the inner ring of electrodes and the outer ring of electrodes is about one quarter of the diameter of the inner ring.

32. An electrode arrangement according to claim 27, wherein the support means comprises a plurality of compartments ($32_1$–$32_{16}$), each comprising a conductive medium for contacting the surface of a volume (12') to be imaged, and lower conductivity partitions ($28_1$–$28_{16}$) between adjacent compartments, each compartment housing a pair of electrodes comprising one electrode from said first group ($S_1$–$S_{16}$) and one electrode from said second group ($R_1$–$R_{16}$).

33. An electrode arrangement according to claim 27, wherein the electrodes are supported in a planar array (60,62), and each electrode of said first group is spaced from an associated electrode of said second group in a direction substantially perpendicular to the plane of the array.

34. An electrode arrangement according to claim 27, wherein the support means (24,26,28,30) is rigid and a conductive interface medium (36) is disposed for juxtaposing between an inner surface of said support means and the surface of the volume (12) to be measured, the interface medium comprising a material that is conformable to contour variations of said surface of the volume.

35. An electrode arrangement according to claim 34, wherein the interface medium material (36) has a conductivity comparable to that of the volume to be measured.

36. An electrode arrangement for an electrical impedance tomography system comprising a plurality of electrodes ($S_1$–$S_{16}$, $R_1$–$R_{16}$) in an array mounted in a support (24,26,28,30) for supporting the electrodes adjacent a surface of a volume (12') to be imaged, wherein the support comprises a plurality of low conductivity sections ($28_1$–$28_{16}$) alternating with a plurality of high conductivity sections ($32_1$–$32_{16}$) so that its conductivity in a direction that, in use, is normal to the surface is significantly greater than its conductivity in a transverse direction, and the electrodes ($R_1$–$R_{16}$, $S_1$–$S_{16}$) are disposed in the high conductivity sections ($32_1$–$32_{16}$), respectively, so as to be spaced, in use, from said surface.

37. An electrode arrangement according to claim 36, wherein the support comprises a plurality of compartments ($32_1$–$32_{16}$), each separated from neighbouring compartments by an insulating partition ($28_1$–$28_{16}$), each compartment comprising a material having a conductivity comparable to the conductivity of the volume the conductivity distribution of which is to be measured and containing at least one of the electrodes.

38. An electrode arrangement for an electrical impedance tomography system comprising an array of electrodes ($S_1$–$S_{16}$, $R_1$–$R_{16}$) fixed spatially relative to each other in a rigid support (24,26,28,30), and an interface medium (36) for interfacing the rigid support to a surface of a volume (12') the conductivity distribution of which is to be measured, the interface medium being conductive so as to connect the electrodes electrically to the surface and pliable so as to conform to variations in relief of the surface.

39. An electrode arrangement according to claim 38, wherein the interface medium material (36) has a conductivity comparable to that of the volume to be measured.

40. An electrical impedance tomograph according to claim 39, wherein the support means comprises a plurality of compartments ($32_1$–$32_{16}$), each comprising a conductive medium for contacting the surface of a volume (12') to be imaged, and lower conductivity partitions ($28_1$–$28_{16}$) between adjacent compartments, each compartment housing a pair of electrodes comprising one electrode from said first group ($S_1$–$S_{16}$) and one electrode from said second group ($R_1$–$R_{16}$).

41. An electrical impedance tomograph comprising a first group of electrodes ($R_1$–$R_{16}$) and a second group of electrodes ($S_1$–$S_{16}$) and support means (24,26,28,30) for supporting the electrodes adjacent a surface of a volume (12') the electrical impedance of which is to be mapped by the system, wherein the first group of electrodes ($R_1$–$R_{16}$) is closer than the second group of electrodes ($S_1$–$S_{16}$) to a part of the support means which, in use, will be adjacent said surface, and further comprising means (16,18,20) for stimulating, sequentially, pairs of electrodes ($S_1$–$S_{16}$) and, for each pair stimulated, measuring corresponding potential differences between a pair or pairs of the remaining electrodes, and processing the measured potentials to map electrical conductivity distribution of a volume (12').

42. An electrical impedance tomograph according to claim 41, wherein each electrode of the first group ($R_1$–$R_{16}$) is substantially aligned with an adjacent electrode of the second group ($S_1$–$S_{16}$) in a direction extending substantially normal, in use, to said surface.

43. An electrical impedance tomograph according to claim 42, wherein the support means (24,26,28,30) comprises an annular structure, the first group of electrodes ($R_1$–$R_{16}$) and the second group of electrodes ($S_1$–$S_{16}$) being arranged in an inner ring and an outer ring, respectively, about a central part of the annular structure.

44. An electrical impedance tomograph according to claim 43, wherein the annular structure (24,26,28,30) is circular and the spacing between the inner ring of electrodes and the outer ring of electrodes is about one quarter of the diameter of the inner ring.

45. An electrical impedance tomograph according to claim 41, wherein the support means (24,26,28,30) comprises an annular structure, the first group of electrodes ($R_1$–$R_{16}$) and the second group of electrodes ($S_1$–$S_{16}$) being arranged in an inner ring and an outer ring, respectively, about a central part of the annular structure.

46. An electrical impedance tomograph according to claim 41, wherein the electrodes are supported in a planar array (60,62), and each electrode of said first group is spaced from an associated electrode of said second group in a direction substantially perpendicular to the plane of the array.

47. An electrical impedance tomograph according to claim 41, wherein the support means (24,26,28,30) is rigid and a conductive interface medium (36) is disposed for juxtaposing between an inner surface of said support means and the surface of the volume (12) to be measured, the interface medium comprising a material that is conformable to contour variations of said surface of the volume.

48. An electrical impedance tomograph according to claim 47, wherein the interface medium material (36) has a conductivity comparable to that of the volume to be measured.

49. An electrical impedance tomograph according to claim 41, wherein the support means (24,26,28,30) has anisotropic conductivity with its conductivity in said direction normal to said surface, in use, being significantly higher than its conductivity in directions transverse thereto.

50. An electrode impedance tomograph according to claim 49, wherein the support means (24,26,28,30) comprises a plurality of higher conductivity sectors (32) alternating with, and defined by, a plurality of lower conductivity regions (28).

51. An electrical impedance tomograph according to claim 41, wherein the support comprises a plurality of low conductivity sections ($28_1$–$28_{16}$) alternating with a plurality of high conductivity sections ($32_1$–$32_{16}$) so that its conductivity in a direction that, in use, is normal to the surface is significantly greater than its conductivity in a transverse direction, and the electrodes ($R_1$–$R_{16}$, $S_1$–$S_{16}$) are disposed in the high conductivity sections ($32_1$–$32_{16}$), respectively, so as to be spaced, in use, from said surface.

52. An electrical impedance tomograph according to claim 51, wherein the support comprises a plurality of compartments ($32_1$–$32_{16}$), each separated from neighbouring compartments by an insulating partition ($28_1$–$28_{16}$), each compartment comprising a material having a conductivity comparable to the conductivity of the volume the conductivity distribution of which is to be measured the containing at least one of the electrodes.

53. An electrical impedance tomograph for use in a method of determining electrical impedance tomography of a conductive volume (12) by selecting, in turn, each of a plurality of pairs of locations (S) upon a surface of the volume (12) and supplying a stimulation current to the surface by way of the selected pair of locations, and recording, for each selected pair, a resulting potential difference between at least one pair (R) of the remaining locations, and processing the recorded potential differences to plot electrical conductivity distribution within said volume comprising:

(i) a plurality of electrodes ($S_1$–$S_{16}$, $R_1$–$R_{16}$) for disposing upon or adjacent said surface, each at a respective one of said plurality of locations;

(ii) means (16) for selecting each pair ($S_1,S_2;S_2,S_3, \ldots S_{15},S_{16}$) of electrodes in turn and applying a stimulation current thereto and, for each particular pair of locations stimulated, the pair or pairs of locations which, if stimulated, would produce an electric field with vectors most closely aligned with the corresponding vectors of the electric field produced by stimulation of said particular pair of locations; and recording the potential difference between each pair of electrodes selected for recordal; and (iii) means (18) for processing the recorded potential differences to determine the electrical impedance tomography for the volume.

* * * * *